United States Patent [19]

Brand

[11] 4,451,651

[45] May 29, 1984

[54] PREPARATION OF ISOCYANURIC ESTERS

[75] Inventor: Johannes Brand, Schalkhaar, Netherlands

[73] Assignee: Akzo NV, Arnhem, Netherlands

[21] Appl. No.: 439,140

[22] Filed: Nov. 4, 1982

[30] Foreign Application Priority Data

Nov. 4, 1981 [NL] Netherlands ............... 8104978

[51] Int. Cl.$^3$ ........................................... C07D 251/34
[52] U.S. Cl. .................................................. 544/221
[58] Field of Search ........................................ 544/221

[56] References Cited

U.S. PATENT DOCUMENTS

| | | | |
|---|---|---|---|
| 3,037,979 | 6/1962 | Fukui et al. | 544/221 |
| 3,088,948 | 5/1963 | Little et al. | 544/221 |
| 4,326,057 | 4/1982 | Cohen et al. | 544/221 |

FOREIGN PATENT DOCUMENTS

| | | | |
|---|---|---|---|
| 2657237 | 7/1977 | Fed. Rep. of Germany . | |
| 1402888 | 5/1965 | France | 544/222 |
| 858810 | 1/1961 | United Kingdom . | |

*Primary Examiner*—John M. Ford
*Attorney, Agent, or Firm*—Stevens, Davis, Miller & Mosher

[57] ABSTRACT

The present invention relates to a process of preparing isocyanuric esters by catalytic isomerization of the corresponding cyanurates in the absence of a solvent that dissolves in the isocyanuric esters. As catalysts there are applied onium or inium salts such as quaternary ammonium and phosphonium compounds.

In particular, the present process is applied in preparing triallyl isocyanurate.

5 Claims, No Drawings

PREPARATION OF ISOCYANURIC ESTERS

The invention relates to a process of preparing isocyanuric esters by catalytic isomerization of the corresponding cyanurates in the absence of a solvent that dissolves in the isocyanuric esters.

Among these esters, the most important are the (iso)-triallyl esters. Either of them can be converted into polymers having useful properties and also may be applied for modifying other polymers. Poly-triallyl isocyanurate displays thermal stability even up to and above a temperature of 400° C.

More particularly, triple esters of isocyanuric acid may be prepared in various ways. In direct preparations the starting material is an alkali cyanate or isocyanuric acid, which in a suitable solvent is reacted with a halide into the ester desired. The purity of the product obtained in solution being insufficient as a result of side reactions, subsequent steps are required comprising evaporation, purification by washing and, finally, distillation.

In view of the laboriousness of these direct methods of preparation also the possibilities of indirect methods have been investigated. In that case the cyanuric ester is prepared in one step, after which the iso compound desired is obtained by isomerization. The above-described uses of cyanuric esters require that these compounds, of which triallyl cyanurate (TAC) is on a large scale produced from cyanuric chloride ($C_3N_3Cl_3$) and allyl alcohol, should be satisfactorily available.

For this isomerization of cyanuric esters the following methods are known:
a. thermal; in the absence of a solvent this reaction proceeds slowly even at elevated temperature (200° C.), so that in this way only esters having a very high thermal stability can be prepared;
b. applying a solvent having a high dielectric constant (Federal German Patent Specification No. 26 57 237), in which case use may be made of a temperature lower than 200° C.; the solvents required, however, are very expensive and this method of preparation is laborious and energy intensive because of the necessary recovery of solvents;
c. catalytic (Balitskaya et al., Uk. Khim. Zh. 40 (8), 1974, p. 881); using metallic copper as catalyst leads to isomerization of TAC to triallyl isocyanurate going to completion within a period of 5 to 25 hours and at a temperature of 30° to 70° C.

Considering that of these isomerization methods the catalytic alternative offers the greatest advantage because of the absence of a solvent which dissolves in the isocyanuric ester this method has been further investigated. Applicant has not succeeded, however, in reproducing the results mentioned by the authors. In the temperature range of 30° to 70° C. no isomerization was observed and upon a further increase in temperature polymerization took place before the reaction mixture could be found to contain any isocyanurate, even if the TAC has previously been stabilized with an inhibitor. None of these methods permit the preparation in one step at a temperature below 200° C. and at a sufficiently high reaction speed of an isocyanurate triester of high purity without the product having to be isolated from a solvent. However, a process has now been found by which in the absence of a solvent which dissolves in the isocyanuric ester, esters of cyanuric acids can in one step be converted into isocyanuric esters.

This novel method of preparing isocyanuric esters from the corresponding cyanurates is characterized in that use is made of a catalyst which satisfies any one of the following formulae:

$$[R_nNH_{4-n}]^+X^-, \tag{1}$$

wherein n=1, 2, 3 of 4,

$$[R_pPH_{4-p}]^+X^-, \tag{2}$$

wherein p=3 of 4,

$$[R'C_5H_4NR'']X^-, \tag{3}$$

wherein $C_5H_4N$ is a pyridine ring, and

$$[R_1R_2R_3S]^+X^-, \tag{4}$$

wherein
X=halogen or hydroxide,
R=an alkyl group having 1–18 carbon atoms, an alkenyl group having 1–18 carbon atoms, a phenyl group or benzyl group, with the compounds 1 and 2 containing not more than one phenyl group or benzyl group,
R'=hydrogen, an alkyl group having 1 to 4 carbon atoms or an alkenyl group having 1 to 4 carbon atoms,
R''=an alkyl group having 1 to 18 carbon atoms, or an alkenyl group having 1 to 18 carbon atoms,
$R_1$, $R_2$ and $R_3$=an alkyl group having 1 to 18 carbon atoms, an alkenyl group having 1 to 18 carbon atoms or phenyl.

At room temperature these catalysts are usually solid substances that do not or hardly dissolve in the esters, but at a temperature in the range of 75° to 200° C. their use leads to a homogeneous liquid reaction mixture, both with the cyanuric esters and with the resulting isocyanurates. A great many of the compounds that are suitable according to the present invention to be used as catalysts are grouped under the heading of "phase-transfer catalysts" and are known as onium or inium salts. In some cases the procedure may be simplified. In actual practice a number of said catalysts, for instance those of the formula: $(R_3NH)^+X^-$, are preferably prepared in aqueous solution. It has been found that the resulting solutions need not undergo any further treatment before they are used in the present process. For, at room temperature these aqueous solutions will not or hardly form a homogeneous mixture with the isocyanuric ester, whereas at elevated temperature they will.

The catalyst also may be prepared in situ by mixing the appropriate starting materials with the cyanuric ester. During heating to isomerization temperature and during isomerization the desired onium or inium salt is formed. The catalyst may be added as such to the reaction components or in the form of an (aqueous) solution. Optionally, the catalyst may previously be prepared from the corresponding starting materials (e.g. $R_3N+RX \rightarrow (R_4N)^+X^-$) in the same reactor as the one in which isomerization takes place.

According to the invention isomerization is preferably carried out as follows:
a cyanuric triester in the presence of at least one of the suitable catalysts, dissolved or not in water, is heated to the reaction temperature which in actual practice is in the range of 75° to 200° C. At a temperature above 100° C. the water which may be present is partly distilled off. Homogenization of the reaction mixture may be promoted by stirring and the mixture may, if desired, be protected from the action of air oxygen while keeping it under a stream of nitrogen. Optionally, polymerization sensitive cyanuric esters may be stabilized with suitable inhibitors.

After completion of isomerization the mixture is cooled down. In the case where the catalyst is added without solvent, it will re-solidify upon cooling, so that the liquid in over 98% pure isocyanuric ester can be isolated in a simple manner. In the procedure where the catalyst is added while in aqueous solution, the mixture will upon cooling separate into two layers: one aqueous layer containing the catalyst and a small amount of isocyanuric ester, and one layer of 98% pure, isomerized endproduct. To enhance the purity of the isomerized ester it can be freed from traces of catalyst by washing with water and subsequent drying. After conversion the solid or water-dissolved catalyst fraction may contain a small proportion of the starting compound and the resulting isomer. However, this catalyst fraction may very well be re-used several times until it requires purification.

The present process may be carried out batchwise, semibatchwise or continuously.

EXAMPLES 1–18

The following table gives the results obtained in examples of preparations carried out in accordance with the invention. For comparison it also gives the results of a few preparations carried out in the absence of a catalyst.

The experiment listed in the table were carried out by allowing the components in the amounts mentioned in the table to react with each other, with stirring, in a reaction flask.

completed after 4 hours, which demonstrates that the present catalyst can be re-used without any problems.

EXAMPLE 20

Into a reaction flask there were charged 7,9 g tri-n-butylamine, 5,0 g allyl bromide and 71,3 g TAC. This mixture was heated to 120° C., with stirring. After 6 hours at that temperature isomerization to triallyl isocyanurate was completed. This example illustrates the in situ preparation of the catalyst before (and during) isomerization.

I claim:

1. A process of preparing isocyanuric esters by catalytic isomerization of the corresponding cyanurates in the absence of a solvent that dissolves in the isocyanuric esters, characterized in that as catalyst one or more compounds of the following formulae are used:

$$[R_nNH_{4-n}]^+X^-, \qquad (1)$$

wherein n = 1, 2, 3 of 4, $$[R_pPH_{4-p}]^+X^-, \qquad (2)$$

wherein p = 3 of 4, $$[R'C_5H_4NR'']^+X^-, \qquad (3)$$

wherein $C_5H_4N$ is a pyridine ring, $$[R_1R_2R_3S]^+X^-, \qquad (4)$$

wherein X = halogen or hydroxide,
R = an alkyl group having 1–18 carbon atoms, an alkenyl group having 1–18 carbon atoms, a phenyl group or benzyl group, with the compounds 1 and 2 containing not more than one phenyl group or benzyl group,

| Example | cyanuric ester type | g | catalyst type | | g | in g water | mol % | reaction temp. °C. | reaction time to complete isomerization hours | Notes |
|---|---|---|---|---|---|---|---|---|---|---|
| 1 | triallyl | 72,0 | tetrabutyl | NBr | 13,9 | | 14,9 | 125 | 4 | |
| 2 | " | 72,0 | none | | | | | 125 | | no isomerization after 7 hours |
| 3 | " | 72,0 | tetrabutyl | NBr | 13,9 | 25,8 | 14,9 | 120 | 11 | |
| 4 | " | 72,0 | " | | 13,9 | 25,8 | 14,9 | 130 | 5 | |
| 5 | " | 72,4 | " | | 5,3 | | 5,7 | 150 | 3 | |
| 6 | " | 72,0 | " | NJ | 16,0 | | 15,0 | 125 | 4 | |
| 7 | " | 72,0 | tributylhexadecyl | PBr | 22.0 | | 15,0 | 120 | 6 | |
| 8 | " | 76,8 | tetrabutyl | PBr | 31,4 | 5,5 | 30,0 | 120 | 9 | |
| 9 | " | 72,0 | tributyl | NHBr | 23,5 | 7,6 | 30,6 | 120 | 9 | |
| 10 | " | 72,0 | trimethyl (C$_{12-14}$) | NCl | 12,1 | 21,4 | 15,1 | 120 | 12 | |
| 11 | " | 72,0 | tri(C$_{8-10}$)methyl | NCl | 17,1 | | 14.7 | 120 | 11 | |
| 12 | " | 70,9 | cetyl pyridinium bromide | | 16,4 | | 15.0 | 120 | 10 | |
| 13 | " | 70,4 | tetrabutyl | NOH | 11,0 | 16,4 | 15,0 | 130 | 8 | |
| 14 | " | 70,0 | triphenyl sulphonium chloride | | 12,7 | 12,7 | 15,1 | 130 | 8 | |
| 15 | di-allyl n-butyl | 68,5 | tetrabutyl | NBr | 24,9 | 4,4 | 29,9 | 120 | 10 | |
| 16 | trimethyl | 14,4 | " | | | 0,7 | 2,5 | 175 | 1 | |
| 17 | trimethyl | 14,4 | none | | | | | 175 | | 10% monomer after 1 hour |
| 18 | tribenzyl | 50,0 | tetrabutyl | NBr | 6,0 | | 14,9 | 165 | 3 | |

EXAMPLE 19

The filter cake isolated upon completion of the isomerization according to Example 1 (=used catalyst) was again employed in the isomerization of TAC according to Example 1. The isomerization again appears to be R' = hydrogen, an alkyl group having 1 to 4 carbon atoms or an alkenyl group having 1 to 4 carbon atoms,
R" = an alkyl group having 1 to 18 carbon atoms, or an alkenyl group having 1 to 18 carbon atoms, R$_1$, R$_2$ and R$_3$=an alkyl group having 1 to 18 carbon atoms, an alkenyl group having 1 to 18 carbon atoms or phenyl.

2. A process according to claim 1, characterized in that triallyl cyanurate is converted into triallyl isocyanurate.

3. A process according to claim 1, characterized in that the catalyst is dissolved in water.

4. A process according to claim 1, characterized in that the reaction is carrid out at a temperature in the range of 75° to 200° C.

5. A process according to claim 1, characterized in that the catalyst is re-used after completion of the reaction and its subsequent isolation from the reaction product.

* * * * *